United States Patent [19]

Whigham

[11] Patent Number: 4,779,617

[45] Date of Patent: Oct. 25, 1988

[54] PACEMAKER NOISE REJECTION SYSTEM

[75] Inventor: Robert H. Whigham, Aurora, Colo.

[73] Assignee: Telectronics N.V., Curacao, Netherlands Antilles

[21] Appl. No.: 915,693

[22] Filed: Oct. 6, 1986

[51] Int. Cl.⁴ ............................................. A61N 1/00
[52] U.S. Cl. ................................ 128/419 P; 128/696
[58] Field of Search ......... 128/419 P, 419 PT, 419 R, 128/901, 419 PG, 696

[56] References Cited

U.S. PATENT DOCUMENTS

| | | | |
|---|---|---|---|
| 3,926,197 | 12/1975 | Alley, III | 128/419 PG |
| 3,939,824 | 2/1976 | Arneson et al. | 128/901 |
| 4,263,919 | 4/1981 | Levin | 128/901 |
| 4,379,459 | 4/1983 | Stein | 128/419 PG |
| 4,408,615 | 10/1983 | Grossman | 128/901 |
| 4,516,579 | 5/1985 | Ivnich | 128/419 PG |
| 4,664,116 | 5/1987 | Shaya et al. | 128/419 PT |

Primary Examiner—Francis J. Jaworski
Assistant Examiner—George Manuel
Attorney, Agent, or Firm—Gottlieb, Rackman & Reisman

[57] ABSTRACT

A noise rejection circuit for an implantable pacemaker. During re-triggerable relative refractory periods following a heartbeat, the peak noise level is sensed; the relative refractory period is re-started whenever the input signal exceeds the previous peak. Following a time-out of the relative refractory period, the peak value detected, representing the noise level, is added to the programmed threshold value; the sum is used as the threshold value during sensing.

16 Claims, 2 Drawing Sheets

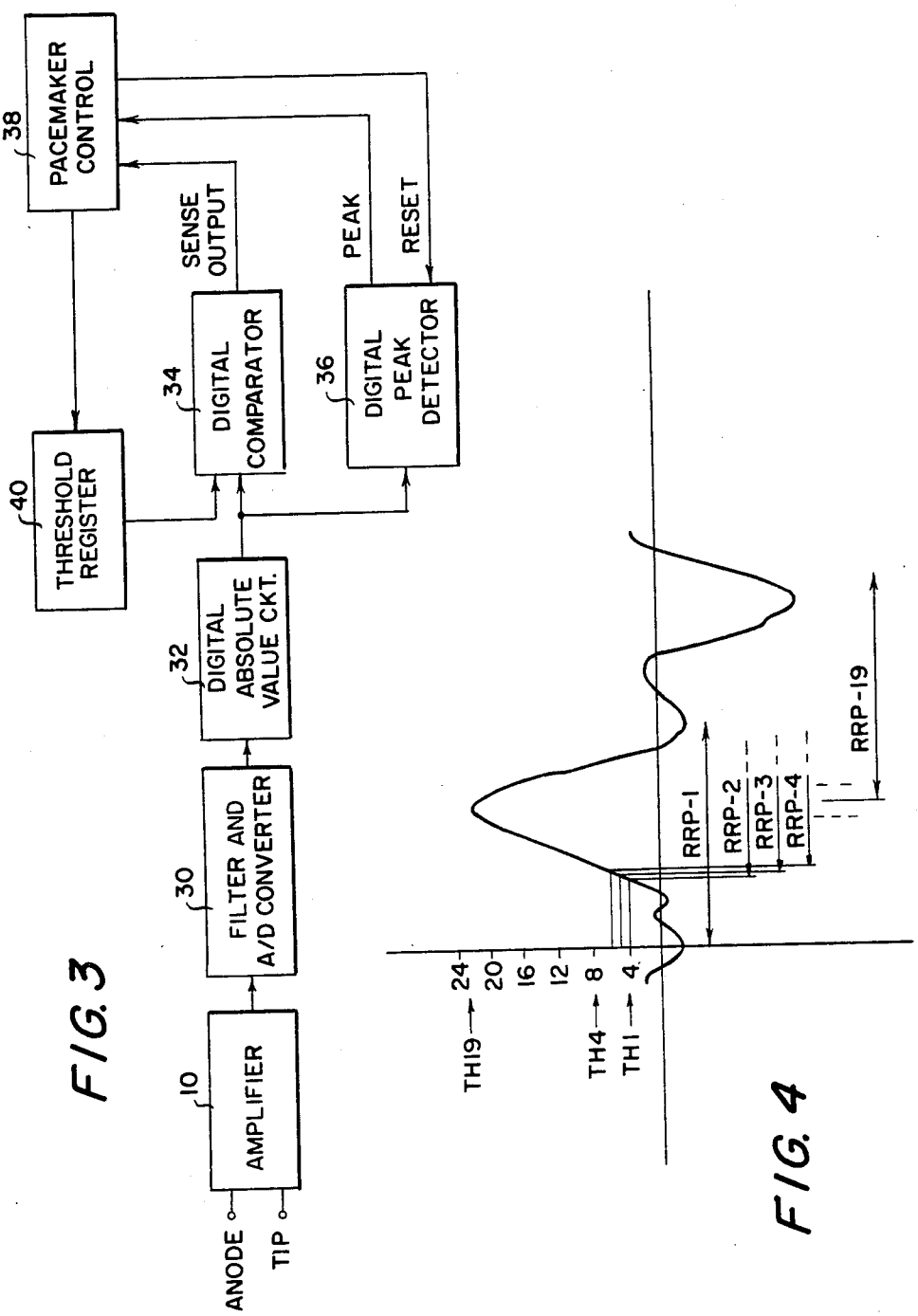

PACEMAKER NOISE REJECTION SYSTEM

DESCRIPTION

This invention relates to implantable pacemakers, and more particularly to systems for rejecting noise which is present in the cardiac signal which is sensed.

A typical modern-day pacemaker is provided with a sense capability as well as a pace capability. Although the present invention has application to any pacemaker sense channel in which noise is to be rejected, the invention can be understood most readily by considering a simple demand VVI pacemaker. The electrodes are used for both delivering a stimulus and for sensing a spontaneous heartbeat. Typically, following a heartbeat, whether it be paced or spontaneous, a sensing interval ensues (usually following an initial time period during which sensing is disabled). If by the end of the sensing interval a spontaneous beat is not sensed, a pacing stimulus is generated. On the other hand, if a spontaneous beat is sensed, then a pacing stimulus is not generated. With a new heartbeat, the cycle repeats.

It is apparent that noise in the sense channel can give rise to erroneous operation. In the worst case, if continuous noise is interpreted by the pacemaker as representing rhythmic heartbeats, no stimuli will be generated even if the heart is not beating properly. It is apparent that mechanisms for discriminating against noise are of great interest in the pacemaker field.

It is a general object of my invention to provide an improved pacemaker noise rejection system.

It is a standard technique to provide absolute and relative refractory periods in a pacemaker to allow the after-potential from a stimulus and/or the heart's evoked response to dissipate. The absolute refractory period (ARP) is a fixed interval which immediately follows a paced or sensed beat, and during which sensing is totally disabled. The relative refractory period (RRP) follows the ARP; during the RRP, the after-potential from the stimulus has dissipated, cardiac signals are quiescent, and noise can be detected. In fact, the purpose of providing the RRP is to allow noise to be detected. A typical pacemaker includes a sensing threshold; any sensed signal whose magnitude is above the threshold is treated as representing a cardiac event. Cardiac events should not be sensed during the RRP, however, because the RRP occurs too soon after a heartbeat. Therefore, if the sensed signal has an amplitude greater than the threshold during the RRP, it is assumed that the signal is noise and the RRP is immediately restarted.

As long as an RRP is in progress, sensing is disabled (other than to verify that noise is present so that the RRP can be re-started). If the RRP is continually re-started, a stimulus will be generated at the end of the inter-beat sensing interval (which is the reciprocal of the rate of the pacemaker).

In the prior art, noise rejection systems have generally involved the making of adjustments to the pacemaker sensitivity. The sensitivity is the magnitude of an input signal which is just sufficient to cause the pacemaker to recognize a cardiac event. By lowering the sensitivity, the effect of noise is reduced because it now requires a higher input signal level in order to exceed the threshold. Typical systems of this type are shown in U.S. Pat. Nos. 4,379,459 and 4,516,579. The main difficulty with prior art schemes is that they are effective only for continuous noise, for example, noise arising from power line effects. The prior art schemes do not reject noise which arises, for example, from the patient's own skeletal muscles. It is known that skeletal muscle noise can give rise to erroneous cardiac event indications.

In accordance with the principles of my invention, the threshold value is adjusted during each cardiac cycle. Following a heartbeat, a relatively low threshold is set. During the first RRP, the noise in the input signal almost certainly causes the threshold to be exceeded. The peak input signal which is sensed during the first RRP is registered and the initial threshold is increased. Another RRP is started and the same thing happens. The process continues with the threshold continuously increasing. Eventually, there is an RRP during which the threshold is not exceeded. The last threshold represents the level of the noise. During the following sensing interval, in which legitimate cardiac activity is expected, the threshold which is used is the desired threshold in the absence of noise plus the previously determined noise level (or some function of it). It is only if this higher threshold is exceeded that it is assumed that a cardiac event has occurred. Because the increment added to the desired threshold is determined on a per-cycle basis, as opposed to the prior art in which the threshold is adjusted only as a function of continuous noise, the noise rejection system of my invention can discriminate against skeletal myopotentials which are not sustained.

Further objects, features and advantages of my invention will become apparent upon consideration of the following detailed description in conjunction with the drawing, in which:

FIG. 3 depicts the illustrative embodiment of my invention; and

FIG. 4 depicts a typical noise signal and will be helpful in explaining how the threshold of the system of FIG. 3 is caused to continuously increase during a single cardiac cycle.

Figure 1A:
FIG. 1A depicts the ARP, RRP and sensing intervals in the absence of noise.

As depicted in FIG. 1A, in a typical pacemaker there is a 150-millisecond absolute refractory period which follows a paced or sensed beat. During the ARP, sensing is totally disabled. There then follows a 100-millisecond relative refractory period. If the input signal does not exceed the threshold level during the RRP, then normal sensing begins. The duration of the sensing interval is determined by the rate of the pacemaker. The total beat-to-beat interval is in the range 500–1050 milliseconds. Taking into account the 250 milliseconds of the refractory periods, the sensing interval is thus in the range 250–800 milliseconds. Typically, if the preceding beat was spontaneous, the sensing interval is a little longer than if the preceding beat was paced, a feature known in the art as hysteresis. During the sensing interval, the pacemaker looks for a natural heartbeat. The pacemaker stimulates the heart only if it times out without detecting a natural beat. A new ARP begins with each heartbeat, whether it is paced or spontaneous.

Figure 1B:
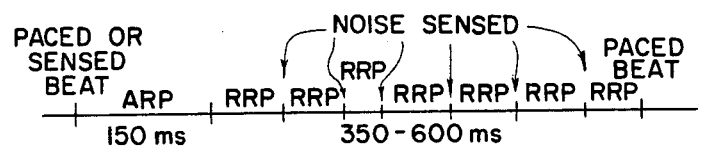
FIG. 1B depicts how an RRP is re-started whenever noise is sensed during a preceding RRP.

The timing diagram of FIG. 1B depicts what happens when noise is sensed during the first and succeeding relative refractory periods. Any input signal greater than the sensing threshold is assumed to be noise, and the RRP is immediately re-started for another 100 milliseconds. If noise is continuously present, as indicated in FIG. 1B, then the sensing function of the pacemaker is continuously inhibited. This is a fail-safe approach that ensures that the heart will be paced, at the end of the sensing interval, in the presence of noise.

It should be noted that in FIG. 1A, the total time which is allowed to elapse from the end of the ARP until the next stimulus is 350–900 milliseconds (the sum of the RRP and the sensing interval). In FIG. 1B, the total interval is only 350–600 milliseconds. There is no sensing which could allow recognition of a heartbeat. The pacemaker generates a stimulus during every cycle. In order to ensure that the stimulus does not occur during the T wave of a spontaneous beat, something which is generally recognized to be dangerous, the beat-to-beat interval is made shorter. It is generally believed that a stimulus which is applied during a T wave can give rise to tachycardia. The pacemaker no longer stays synchronized to the natural rhythm; it paces faster than normal to ensure that its stimuli capture the heart.

The actual timing mechanisms of a pacemaker are not important insofar as the present invention is concerned. What is important is that noise be recognized for what it is. Referring to FIGS. 1A and 1B, it will be apparent that if an RRP elapses without any noise being sensed, then the sensing interval will commence. If noise is now present at the input, it will be treated as a cardiac event even though such an event may not have taken place. That is why it is important that there be a way to discriminate against noise which occurs during the sensing interval. The key feature of my invention is that the noise which occurs during the relative refractory periods is analyzed and used later in the same cycle to reject noise which occurs during the sensing interval. [The straight-forward approach would be to use a filter to filter out the frequencies associated with skeletal myopotentials. Unfortunately, these same frequencies characterize cardiac potentials as well, and any filter employed would filter out the good signals with the bad.]

Figure 2A:
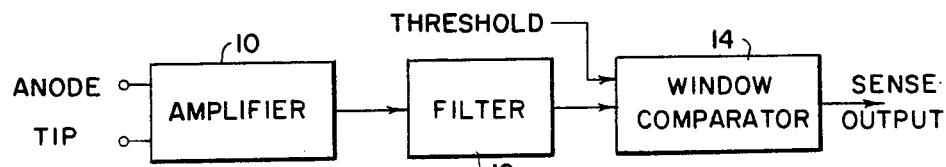
FIGS. 2A-2C depict three prior art systems which will be helpful in understanding the approaches which have been taken to reject noise in the prior art.
Figure 2B:
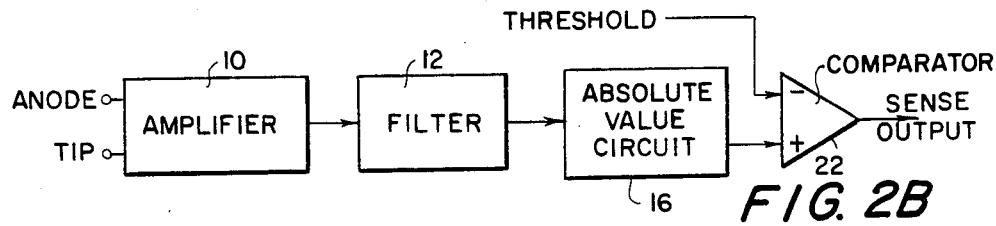

The simplest approach to rejecting noise is shown in FIG. 2A. The cardiac signal between the anode and the tip electrodes is amplified in amplifier 10 and then filtered in filter 12 so that only cardiac frequencies of interest remain. The signal is then applied to an input of window comparator 14. A threshold level is also applied to the window comparator. The window comparator typically consists of an absolute value circuit and a unipolar comparator as shown in FIG. 2B. The absolute value circuit 16 generates an output which is the absolute value of the input. In this way, the maximum excursion in the signal can be operated upon no matter what the direction. When the signal at the plus input of comparator 22 is greater than the signal at the minus input, the sense output goes high to indicate that the absolute magnitude of the input signal has exceeded the threshold. In the circuit of FIG. 2A, the threshold signal really represents two thresholds, one in a positive direction and one in the negative, the two thresholds defining a window between them. It is not known whether the peak signal will be positive or negative, and thus a mechanism must be provided for determining that a cardiac event has occurred if the peak excursion has exceeded a threshold in either direction. The use of an absolute value circuit and a unipolar comparator in the system of FIG. 2B simplifies the circuitry.

Figure 2C:
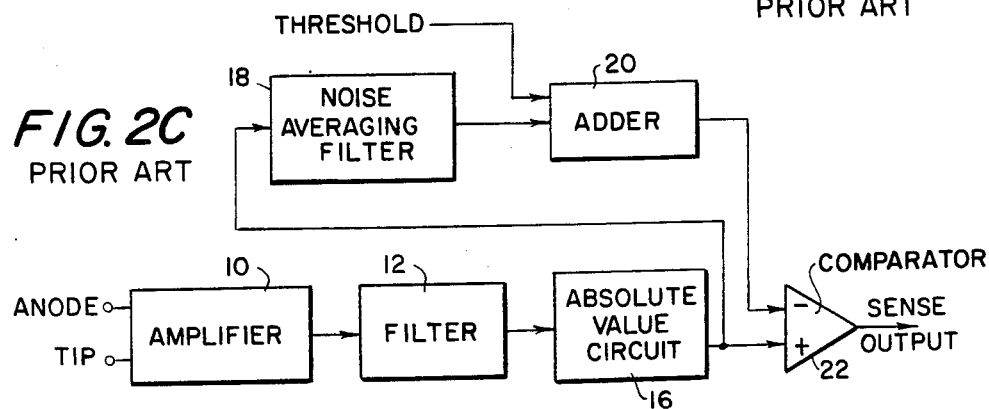

The prior art circuit of FIG. 2C is based on that of FIG. 2B. The output of the absolute value circuit is once again extended to the plus input of comparator 22. But instead of the threshold being applied directly to the minus input, adder 20 adds an increment to the threshold. The increment is the average of the output of the absolute value circuit. Filter 18 derives the average value of the output of circuit 16 so that it can be added to the threshold. In effect, what is being done to move the threshold above the noise level by adding the average noise level to the threshold which would otherwise have been used. Filter 12 eliminates high-frequency noise, and filter 18 operates on the remaining low-frequency noise. In the presence of continuous noise, the output of filter 18 can be meaningful and by adding it to the threshold level set by the physician, in effect the sensitivity of the pacemaker is reduced, that is, a larger input signal is required in order for a cardiac event to be recognized.

In the absence of a true cardiac signal, the threshold furnished to the comparator is above the level of the continuous noise so that the noise is not detected. A natural cardiac signal, which might, for example, ride up and down on 60-Hz noise, will sometimes—but not always—project above the threshold and thus keep the pacemaker in synchronism with the natural rhythm of the heart. Although some cardiac signals are not sensed because the threshold is higher than it otherwise would be, in the usual case enough beats are sensed to keep the pacemaker in syncronism with the natural rhythm. The disadvantage of the approach of FIG. 2C is that it is effectively only for continuous noise such as that from a power line. The technique is not effective to discriminate against the patient's own skeletal muscle noise; in such a case there is no "average" value to speak of and the threshold is not increased from the level set by the physician.

The illustrative embodiment of my invention is shown in FIG. 3. In order to implement the system digitally the individual sub-systems are digital in nature, but many of the functions are similar to those of the prior art systems. Block 30 is a combined filter and analog-to-digital converter. (For particular circuitry which can be employed in a digital system of the type under discussion, reference may be made to the application of Whigham et al, filed on Aug. 1, 1986 and entitled "Pacing Pulse Compensation," and the application of Whigham filed on Aug. 1, 1986 and entitled "Combined Pacemaker Delta Modulator and Brandpass Filter.") Circuit 32 derives the absolute value of the input signal and delivers it to digital comparator 34. The functions performed by blocks 10, 30, 32 and 34 in FIG. 3 are comparable to those performed by blocks 10, 12, 16 and 22 in the prior art circuit of FIG. 2C.

In the co-pending application of Whigham et al, filed on even date herewith and entitled "Automatic Sensitivity Control for a Pacemaker," there is disclosed a system entailing the use of a digital peak detector such as that of block 36 of FIG. 3. That application, however, concerns the automatic control of sensitivity, whereas the subject invention deals with the rejection of noise. The system of each application can utilize the invention of the other, and the two inventions are not shown embodied in the same system only for the sake of clarity. At the end of the ARP of FIG. 1B, pacemaker control 38 resets peak detector 36. It also causes threshold register 40 to be set with a low value, a value slightly above the digitization noise of the analog-to-digital converter. (The exact value is of relatively little importance, as will soon become apparent.) The sense output of comparator 34 goes high whenever the input from circuit 32 is equal to or greater than the threshold level. A new sample is delivered by block 32 every 2 milliseconds in a typical embodiment of the invention and with reference to the implementations referred to above.

During the first RRP, since the threshold level is arbitrarily low, in all likelihood the sense output of comparator 34 will go high. The RRP is immediately re-started as shown in FIG. 1B. Because there is a finite time interval between samples, e.g., 2 milliseconds, the sample value furnished to comparator 34 will usually be greater than or equal to the threshold value as long as the noise at the input is increasing. Consequently, when the sense output of comparator 34 goes high, the peak registered by peak detector 36 will actually exceed the threshold value by the value of one or more digitization steps. (If samples from block 32 can have values from 0 through 31, steps of 1 would equal one digitization step.)

When the sense output of comparator 34 goes high, the new peak value plus one is stored in the threshold register 40. In all likelihood, after another 2 milliseconds have elapsed, the next sample will similarly equal or exceed the new threshold value.

This is shown in FIG. 4. Although block 32 serves to rectify the input signal, it is shown unrectified in FIG. 4 in order that the events be keyed to the actual input signal. With a digitization noise level of 1, the initial threshold value TH1 (on the vertical axis) is set equal to 4, a relatively low level but one which is above the digitization noise. (There is no desire to trigger on digitization noise, that is, noise which is always present.) The first RRP, shown as RRP-1 in the drawing, begins at the end of the ARP. When the noise rises to the TH1 threshold level, the RRP is re-started, indicated by the notation RRP-2. The peak value may be equal to 4 or it may be higher, depending upon the actual value of the input when the sense output of comparator 34 goes high. As shown in FIG. 4, it is assumed that the peak value is equal to 4 and thus the threshold at the start of RRP-2 is equal to 4 plus 1, or 5. As shown in FIG. 4, 2 milliseconds later the peak has risen to a level of 5 when the sense output of comparator 34 goes high. The threshold level stored in register 40 is thus increased again, to 6. It should be noted that the successive peaks can only increase. It is a measured peak plus 1 which is stored in register 40, and a new peak is used by pacemaker control 38 (during the RRP) only if the output of comparator 34 goes high; this, in turn, means that the input signal exceeds the previously stored peak.

The threshold value stays the same or increases each time the RRP is re-started. Eventually, as indicated in FIG. 4, an RRP, in this case RRP-19, is re-started and during that RRP the sense output of comparator 34 does not go high. The previous peak, TH19 in FIG. 4, is a measure of the peak noise detected during the extended RRP. Pacemaker control 38 adds this peak value to whatever value the physician has programmed for the threshold, and it is the sum which is stored in register 40 and used during the sensing interval to determine if a cardiac event has occurred. The maximum instantaneous noise level determined during the RRP is added to the "normal" threshold for use during the sensing interval.

In the event of a very noisy input, the threshold level might rise all the way to the maximum value of 31, but because the output of the comparator goes high when the input equals the threshold, the sense output would go high continuously and the RRP would never time out. No cardiac event would be sensed. On the other hand, if the noise is not excessive, when the threshold level just exceeds the peak of the noise the comparator output will remain low for the duration of an RRP, following which the value stored in the peak detector will be added to the normal threshold value and the sum will be used as the threshold level during the sensing interval.

Although the invention has been described with reference to a particular embodiment it is to be understood that this embodiment is merely illustrative of the application of the principles of the invention. Numerous modifications may be made therein and other arrangements may be devised witout departing from the spirit and scope of the invention.

I claim:

1. An implantable cardiac medical device comprising means for sensing a cardiac signal, means for comparing the sensed cardiac signal with a variable threshold level, means for setting an initial threshold level responsive to the occurrence of a heartbeat, means for timing a re-triggerable relative refractory period, means responsive to said sensed cardiac signal exceeding said threshold level during said relative refractory period for re-triggering the relative refractory period timing and for increasing the threshold level, means responsive to a time-out of the relative refractory period without said sensed cardiac signal exceeding said threshold level for initiating a heartbeat sensing interval, means operative at the start of a heartbeat sensing interval for setting a threshold value equal to a predetermined value increased by a function of said threshold level at the end of the preceding relative refractory period, and means responsive to said sensed cardiac signal exceeding the threshold value during a heartbeat sensing interval for determining the occurrence of a heartbeat.

2. An implantable cardiac medical device in accordance with claim 1 further including means operative subsequent to the determination of the occurrence of a heartbeat for timing an absolute refractory period during which said cardiac signal is not sensed, said re-triggerable relative refractory period following said absolute refractory period.

3. An implantable cardiac medical device comprising means for sensing a cardiac signal, means for comparing the sensed cardiac signal with a variable threshold level, means for setting an initial threshold level responsive to the occurrence of a heartbeat and for successively increasing the threshold level to a final value as the sensed cardiac signal increases until the final threshold level represents the noise level in said sensed cardiac signal, means responsive to said final threshold level representing the noise level in said sensed cardiac signal for initiating a heartbeat sensing interval, means operative at the start of a heartbeat sensing interval for setting a threshold value which is a function of said final threshold level, and means responsive to the sensed cardiac signal exceeding said threshold value during a heartbeat sensing interval for determining the occurrence of a heartbeat.

4. An implantable cardiac medical device in accordance with claim 3 further including means operative subsequent to the determination of the occurrence of a heartbeat for timing an absolute refractory period during which said cardiac signal is not sensed, said increasing means increasing said threshold level as the sensed cardiac signal increases only following said absolute refractory period.

5. An implantable cardiac medical device comprising means for sensing a cardiac signal, means responsive to the determination of the occurrence of a heartbeat for deriving a signal representative of the noise level in said cardiac signal as a function of the cardiac signal only subsequent to such heartbeat, means responsive to derivation of said noise level representative signal for setting a threshold value which is a function thereof and for initiating a sensing interval, and means responsive to said cardiac signal exceeding said threshold value during said sensing interval for determining the occurrence of a heartbeat.

6. An implantable cardiac medical device in accordance with claim 5 further including means for disabling sensing of said cardiac signal during an absolute refractory period which follows the occurrence of a heartbeat, and wherein said signal deriving means operates during a re-triggerable relative refractory period which follows said absolute refractory period.

7. An implantable cardiac medical device in accordance with claim 6 wherein said signal deriving means sets a relatively low repesentative signal at the start of said re-triggerable relative refractory period and increases said representative signal responsive to said cardiac signal exceeding said representative signal during said relative refractory period.

8. An implantable cardiac medical device in accordance with claim 7 wherein said signal deriving means re-triggers said relative refractory period responsive to said cardiac signal being at least equal to said representative signal.

9. A method for determining the occurrence of a heartbeat comprising the steps of sensing a cardiac signal, comparing the sensed cardiac signal with a variable threshold level, setting an initial threshold level responsive to the occurrence of a heartbeat, timing a retriggerable relative refractory period, re-triggering the relative refractory period timing and increasing the threshold level responsive to said sensed cardiac signal exceeding said threshold level during said relative refractory period timing, initiating a heartbeat sensing interval responsive to a time-out of the relative refractory period without said sensed cardiac signal exceeding said threshold level, at the start of a heartbeat sensing interval setting a threshold value equal to a predetermined value increased by a function of said threshold level at the end of the preceding relative refractory period, and determining the occurrence of a heartbeat responsive to said sensed cardiac signal exceeding the threshold value during a heartbeat sensing interval.

10. A method in accordance with claim 9 further including the step of timing an absolute refractory period subsequent to the determination of the occurrence of a heartbeat during which said cardiac signal is not sensed, said relative refractory period following said absolute refractory period.

11. A method for determining the occurrence of a heartbeat comprising the steps of sensing a cardiac signal, comparing the sensed cardiac signal with a variable threshold level, setting an initial threshold level responsive to the occurrence of a heartbeat and successively increasing the threshold level to a final value as the sensed cardiac signal increases until the final threshold level represents the noise level in said sensed cardiac signal, initiating a heartbeat sensing interval responsive to said final threshold level representing the noise level in said sensed cardiac signal, at the start of a heartbeat sensing interval setting a threshold value which is a function of said final threshold level, and determining the occurrence of a heartbeat responsive to the sensed cardiac signal exceeding said threshold value during a heartbeat sensing interval.

12. A method in accordance with claim 11 further including the step of timing an absolute refractory period subsequent to the determination of the occurrence of a heartbeat during which said cardiac signal is not sensed, said threshold level being increased as the sensed cardiac signal increases only following said absolute refractory period.

13. A method for determining the occurrence of a heartbeat comprising the steps of sensing a cardiac signal, responsive to the determination of the occurrence of a heartbeat deriving a signal representative of the noise level in said cardiac signal as a function of the cardiac signal only subsequent to such heartbeat, setting a threshold value which is a function of the derived representative signal and initiating a sensing interval, and determining the occurrence of a heartbeat responsive to said cardiac signal exceeding said threshold value during said sensing interval.

14. A method in accordance with claim 13 further including the step of disabling sensing of said cardiac signal during an absolute refractory period which follows the occurrence of a heartbeat, said signal deriving step being performed during a re-triggerable relative refractory period which follows said absolute refractory period.

15. A method in accordance with claim 14 wherein in said signal deriving step a relatively low representative signal is set at the end of said absolute refractory period and is increased responsive to the amplitude of said cardiac signal exceeding said representative signal during said relative refractory period.

16. A method in accordance with claim 15 wherein in said signal deriving step said relative refractory period is re-triggered responsive to the amplitude of said cardiac signal being at least equal to said representative signal.

* * * * *